(12) United States Patent
Sezan et al.

(10) Patent No.: US 9,955,939 B2
(45) Date of Patent: May 1, 2018

(54) STETHOSCOPE SYSTEM INCLUDING A SENSOR ARRAY

(71) Applicant: QUALCOMM Incorporated, San Diego, CA (US)

(72) Inventors: Muhammed Ibrahim Sezan, Los Gatos, CA (US); Eugene Dantsker, San Diego, CA (US); Kenneth Kaskoun, La Jolla, CA (US); Brian David Niznik, San Diego, CA (US); Christopher Talbot, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days. days.

(21) Appl. No.: 15/013,896

(22) Filed: Feb. 2, 2016

(65) Prior Publication Data

US 2017/0215835 A1    Aug. 3, 2017

(51) Int. Cl.
*A61B 7/04* (2006.01)
*A61B 5/00* (2006.01)
(Continued)

(52) U.S. Cl.
CPC ............. *A61B 7/04* (2013.01); *A61B 5/0205* (2013.01); *A61B 5/08* (2013.01); *A61B 5/721* (2013.01); *A61B 7/00* (2013.01); *A61B 7/026* (2013.01); *A61B 5/6833* (2013.01); *A61B 2562/0204* (2013.01); *A61B 2562/046* (2013.01)

(58) Field of Classification Search
CPC ......... A61B 7/04; A61B 5/024; A61B 5/7203; A61B 2562/0204; A61B 2562/0219;
(Continued)

(56) References Cited

U.S. PATENT DOCUMENTS 6,385,473 B1    5/2002  Haines et al.
8,591,430 B2   11/2013  Amurther et al.
(Continued)

FOREIGN PATENT DOCUMENTS

WO    WO9405207 A1    3/1994

OTHER PUBLICATIONS

Mirza Saquib us Sawar, Transparent and Conformal 'Piezolonic' Touch Sensor, 2015, Electroactive Polymer Actuator and Devices.*
(Continued)

*Primary Examiner* — Norman Yu
(74) *Attorney, Agent, or Firm* — Weaver Austin Villeneuve & Sampson LLP

(57) ABSTRACT

A stethoscope system may include an array of sensors, which may include pressure sensors. The array may be implemented in a wearable "patch" that is conformable to a patient's body. The stethoscope system may include a control system that is capable of receiving signals from the array of sensors. The signals may, for example, correspond to measurements from multiple pressure sensors of the array. The control system may be capable of combining signals from multiple pressure sensors to produce combined signals. The control system may be capable of filtering the combined signals to remove, at least in part, breathing signal components and to produce filtered signals. The control system may be capable of determining a correspondence between heart signal components of the filtered signals and corresponding heart valve activity.

30 Claims, 12 Drawing Sheets

(51) Int. Cl.
*A61B 7/00* (2006.01)
*A61B 5/0205* (2006.01)
*A61B 5/08* (2006.01)
*A61B 7/02* (2006.01)
*A61B 5/02* (2006.01)
*A61B 5/04* (2006.01)

(58) Field of Classification Search
CPC ............ A61B 2562/046; A61B 5/6801; A61B 5/7257; A61B 5/7282; A61B 5/7405; A61B 7/02; A61B 7/026; A61B 2560/0412; A61B 5/0006; A61B 5/02; A61B 5/02007; A61B 5/0205; A61B 5/021; A61B 5/026; A61B 5/029; A61B 5/0402; A61B 5/0452; A61B 5/1118; A61B 5/113; A61B 5/7225; A61M 1/3639; A61M 2205/3331; A61M 2230/06; A61M 2230/40
USPC ........... 381/67; 600/528, 301, 485, 514, 586
See application file for complete search history.

(56) References Cited

U.S. PATENT DOCUMENTS

| | | | |
|---|---|---|---|
| 2005/0043643 A1* | 2/2005 | Priemer | A61B 7/023 600/528 |
| 2007/0055151 A1* | 3/2007 | Shertukde | A61B 5/02007 600/437 |
| 2008/0013747 A1* | 1/2008 | Tran | A61B 5/0295 381/67 |
| 2011/0137209 A1* | 6/2011 | Lahiji | A61B 7/026 600/586 |
| 2012/0220835 A1 | 8/2012 | Chung | |
| 2013/0116584 A1 | 5/2013 | Kapoor | |
| 2013/0237862 A1 | 9/2013 | Song et al. | |
| 2014/0018703 A1* | 1/2014 | Wolfe | A61B 5/024 600/586 |
| 2015/0164340 A1 | 6/2015 | Bedingham et al. | |

OTHER PUBLICATIONS

International Search Report and Written Opinion—PCT/US2016/065934—ISA/EPO—dated Apr. 7, 2017.

* cited by examiner

FIGURE 8A
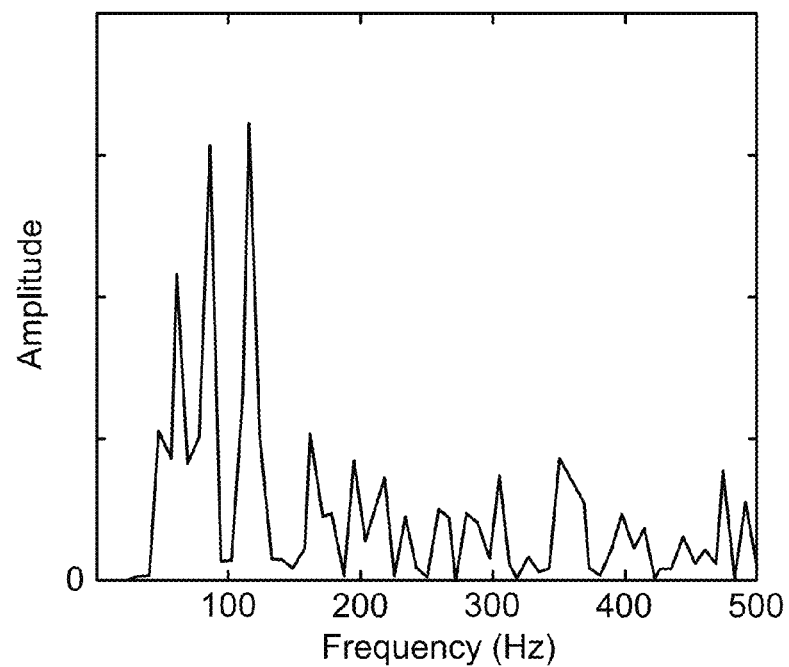
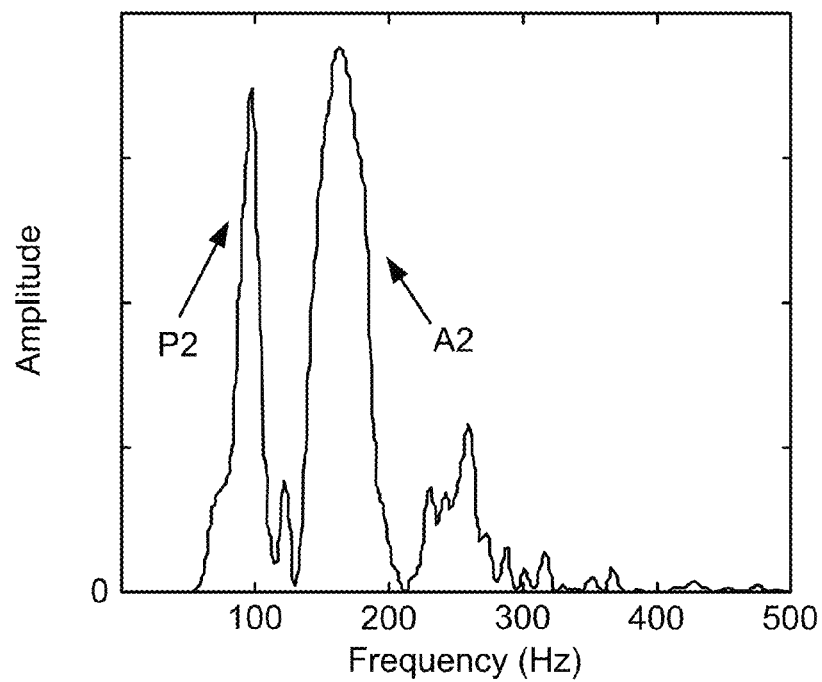
FIGURE 8B

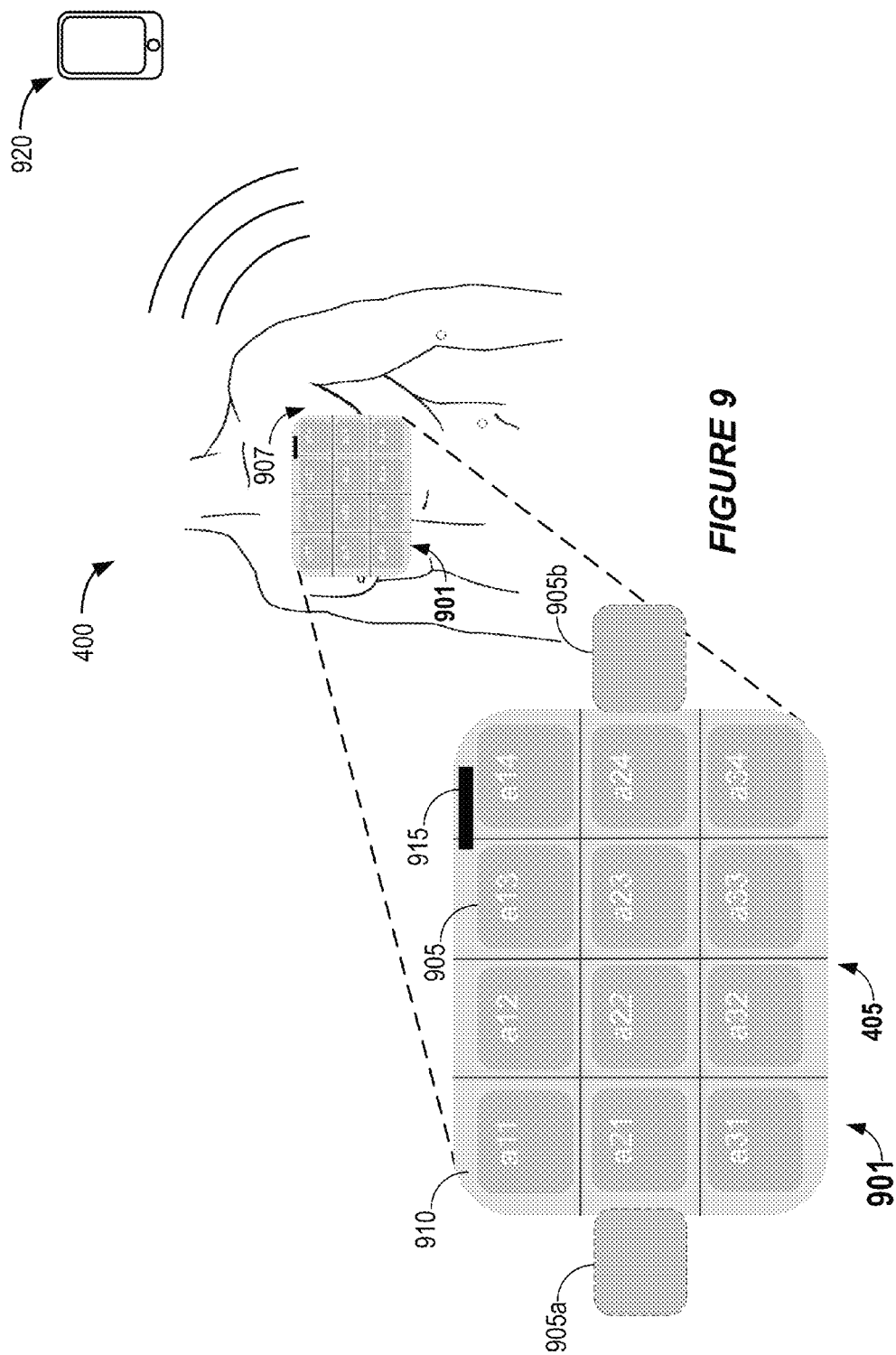

STETHOSCOPE SYSTEM INCLUDING A SENSOR ARRAY

TECHNICAL FIELD

This disclosure relates generally to mobile health devices, methods and systems.

DESCRIPTION OF THE RELATED TECHNOLOGY

Stethoscopes are used by physicians to monitor vibrations in a patient's chest, particularly vibrations associated with heart movements and breathing. Stethoscopes may be capable of detecting such vibrations as sounds or as electrical signals transduced by electromechanical or piezoelectric sensors. Although existing stethoscopes provide generally adequate performance, improved devices would be desirable.

SUMMARY

The systems, methods and devices of the disclosure each have several innovative aspects, no single one of which is solely responsible for the desirable attributes disclosed herein.

One innovative aspect of the subject matter described in this disclosure can be implemented in an apparatus that may include a patch and a control system. The apparatus may be, or may include, a stethoscope system. The patch may include an array of pressure sensors. The patch may be conformable to a patient's body. In some examples, the array of pressure sensors may include identical, or substantially identical, pressure sensors. In some instances, the array of pressure sensors may be a two-dimensional M by N or M by M array, wherein M and N are integers. In some implementations, the patch may include flexible material to which the array of pressure sensors may be attached. In some examples, the patch may include at least one layer of adhesive material for secure placement on the patient's body.

The control system may be capable of receiving signals from the array of pressure sensors. The signals may correspond to measurements from multiple pressure sensors of the array of pressure sensors. In some examples, the signals may correspond to redundant measurements from multiple pressure sensors of the array of pressure sensors. In some instances, the signals may correspond to multiple simultaneous measurements obtained from different areas of a patient's chest during a time interval. In some implementations, the signals may correspond to multiple simultaneous and redundant measurements of vibrations produced by one or more heart valves.

In some implementations, the control system may be capable of combining signals from multiple pressure sensors of the array of pressure sensors to produce combined signals. According to some such implementations, the control system may be capable of performing signal pre-processing before combining the signals. The control system may be capable of filtering the combined signals to remove, at least in part, breathing signal components and to produce filtered signals. In some examples, the control system may be capable of transforming the signals from a time domain into a frequency domain.

According to some implementations, the control system may be capable of determining a correspondence between heart signal components of the filtered signals and corresponding heart valve activity. In some examples, the control system may be capable of determining a correspondence between heart signal components and corresponding parts of a cardiac cycle. In some instances, the control system may be capable of determining heart valve activity based, at least in part, on the filtered signals.

In some examples, the control system may be capable of determining a quality metric for one or more of the heart signal components. Some implementations of the apparatus may include a user feedback system. For example, the user feedback system may include force feedback elements. In some instances, the force feedback elements may be instances of the pressure sensors. According to some implementations, the force feedback elements and the pressure sensors may be piezoionic devices. In some implementations, the control system may be capable of providing instructions (e.g., via the user feedback system) based on a comparison of the quality metric and a quality metric threshold.

In some implementations, the apparatus may include an interface system. According to some such implementations, the control system may be capable of receiving instructions from a second device, via the interface system, and of controlling at least a portion of the apparatus according to the instructions. Accordingly, in some implementations the control system may be disposed, at least in part, in a second device. In some examples, the control system may be capable of detecting an abnormality of heart valve activity and of transmitting a signal, via the interface system, corresponding to the abnormality. In some instances, the interface system may include an interface capable of wireless communication.

Other innovative aspects of the subject matter described in this disclosure can be implemented in a method. The method may involve processing signals from a stethoscope system. In some examples, the method may be performed by a control system. The method may involve receiving, by the control system, signals from an array of pressure sensors. The signals may correspond to measurements from multiple pressure sensors of the array of pressure sensors. The method may involve combining, via the control system, signals from multiple pressure sensors of the array of pressure sensors to produce combined signals. The method may involve filtering the combined signals to remove, at least in part, breathing signal components and to produce filtered signals.

In some implementations, the method may involve determining a correspondence, via the control system, between heart signal components of the filtered signals and corresponding heart valve activity. According to some examples, the method may involve determining a correspondence between heart signal components and corresponding parts of a cardiac cycle. In some instances, the method may involve determining heart valve activity based, at least in part, on the filtered signals.

In some examples, the method may involve determining a quality metric for one or more of the heart signal components. Some implementations of the method may involve providing instructions based on a comparison of the quality metric and a quality metric threshold. In some implementations, the method may involve detecting an abnormality of heart valve activity and transmitting a signal corresponding to the abnormality.

Some or all of the methods described herein may be performed by one or more devices according to instructions (e.g., software) stored on one or more non-transitory media. Such non-transitory media may include memory devices such as those described herein, including but not limited to random access memory (RAM) devices, read-only memory (ROM) devices, etc. Accordingly, other innovative aspects of the subject matter described in this disclosure can be implemented in one or more non-transitory media having software stored thereon.

In some instances, the software may include instructions for receiving, by a control system, signals from an array of pressure sensors. The signals may correspond to measurements from multiple pressure sensors of the array of pressure sensors. The software may include instructions for combining signals from multiple pressure sensors of the array of pressure sensors to produce combined signals. In some examples, the software may include instructions for filtering the combined signals, via the control system, to remove, at least in part, breathing signal components and to produce filtered signals. The software may include instructions for determining a correspondence, via the control system, between heart signal components of the filtered signals and corresponding heart valve activity.

According to some examples, the software may include instructions for determining a quality metric for one or more of the heart signal components. In some such examples, the software may include instructions for providing a response that corresponds with the quality metric. In some implementations, the software may include instructions for detecting an abnormality of heart valve activity and of transmitting a signal corresponding to the abnormality.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

FIG. 8A shows an example of a frequency spectrum for S1 heart sounds.

FIG. 8B shows an example of a frequency spectrum for S2 heart sounds.

FIG. 9 shows an example of a stethoscope system.

DETAILED DESCRIPTION

Figure 1:
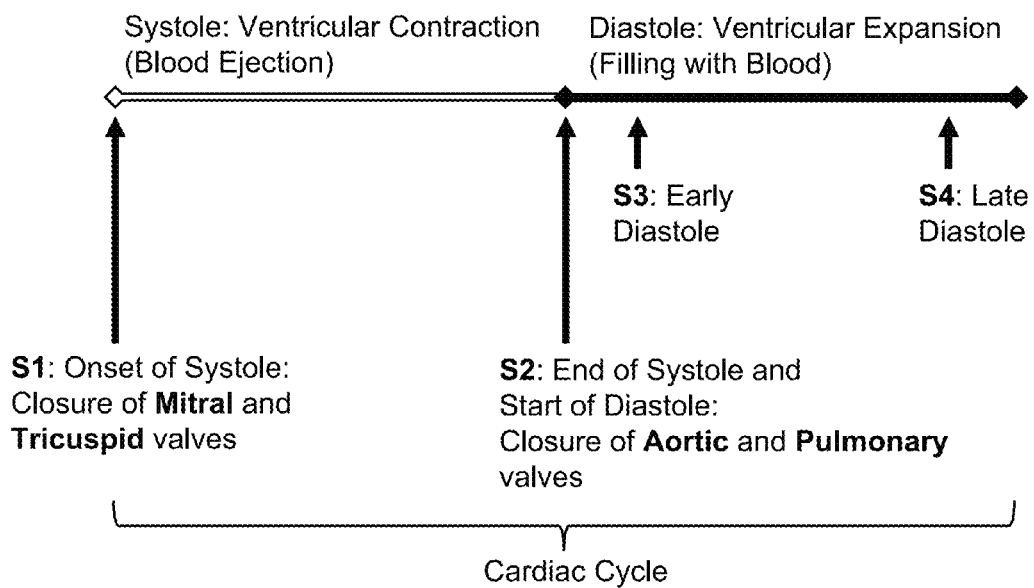
FIG. 1 shows examples of cardiac cycle elements.

The following description is directed to certain implementations for the purposes of describing the innovative aspects of this disclosure. However, a person having ordinary skill in the art will readily recognize that the teachings herein may be applied in a multitude of different ways. For example, one or more components of a stethoscope system may be included in wearable devices, garments or other apparel, including but not limited to smart clothing. It is contemplated that the described stethoscope system implementations may be included in or associated with a variety of electronic devices such as, but not limited to: laptops, mobile telephones, multimedia Internet enabled cellular telephones, mobile television receivers, wireless devices, smartphones, Bluetooth® devices, personal data assistants (PDAs), wireless electronic mail receivers, hand-held or portable computers, netbooks, notebooks, smartbooks, tablets, global positioning system (GPS) receivers/navigators, cameras, camcorders, wrist watches, electronic reading devices (e.g., e-readers), mobile health devices, etc. In some implementations, one or more components of a stethoscope system may be included in furniture. In some examples, one or more components of a stethoscope system may be included in a vehicle. The teachings herein also may be used in applications such as, but not limited to, electronic switching devices, radio frequency filters, sensors, including but not limited to biometric sensors, accelerometers, gyroscopes, motion-sensing devices, magnetometers, inertial components for consumer electronics, parts of consumer electronics products, varactors, liquid crystal devices, electrophoretic devices, etc. Thus, the teachings are not intended to be limited to the implementations depicted solely in the Figures, but instead have wide applicability as will be readily apparent to one having ordinary skill in the art.

Some implementations described in this disclosure can be implemented in a stethoscope system that may include an array of sensors. In some examples, the sensors may include pressure sensors. In some examples, the sensor array may be implemented in a wearable "patch" that is conformable to a patient's body. In some implementations, the patch may be included in a sleeve, in a wrap or in another type of clothing or accessory. In other implementations, the patch may be embedded in furniture, in a medical probe, etc. The stethoscope system may include a control system that is capable of receiving signals from the array of sensors. The signals may, for example, correspond to multiple simultaneous measurements from multiple pressure sensors of the array. The multiple simultaneous measurements may include redundant measurements. The control system may be capable of distinguishing breathing signal components from heart signal components. In some examples, the control system may be capable of determining correlations and/or diversity of signal components. The control system may be capable of filtering the signals to remove, at least in part, the breathing signal components. The control system may be capable of determining a correspondence between heart signal components and corresponding heart valve activity. In some implementations, the control system may be capable of determining a correspondence between heart signal components and corresponding parts of a cardiac cycle. Some implementations may involve combining signals from multiple pressure sensors of the array.

Particular implementations of the subject matter described in this disclosure can be implemented to realize one or more of the following potential advantages. Unlike other stethoscope systems, the stethoscope system disclosed herein enables the user to place a patch that includes the array of pressure sensors and to receive satisfactory heart signal components without requiring the user to have knowledge of the precise location to place the stethoscope system.

For example, some stethoscope systems may include a wearable patch that may be placed across a significant portion of a patient's chest. Some such stethoscope systems may be relatively easier to use than prior art stethoscopes that were intended for use by physicians. Therefore, some stethoscope systems disclosed herein may be more suitable, as compared to prior art stethoscopes, for use in a home, pharmacy or kiosk setting. Some stethoscope systems may be capable of providing information regarding a patient's cardiac activity to the patient, to a doctor or to a family member. In some examples, a stethoscope system may be capable of detecting an abnormality of cardiac activity and of transmitting a signal, via the interface system, corresponding to the abnormality. Some stethoscope systems may be capable of providing continuous, or substantially continuous, measurements of a patient's cardiac activity throughout the day. Such implementations may lead to quicker diagnosis of a patient's abnormal cardiac activity.

Stethoscopes are used by physicians to monitor vibrations in a patient's chest, such as vibrations associated with heart movements and breathing. As noted above, stethoscopes may be capable of detecting such vibrations as sounds or as electrical signals transduced by electromechanical or piezoelectric sensors, such as pressure sensors. Therefore, although heart-related vibrations may sometimes be referred to herein as "heart sounds" and breathing-related vibrations may sometimes be referred to herein as "breathing sounds," such vibrations will not necessarily be detected as sounds.

Heart sounds include sounds generated by the beating heart and the resulting flow of blood through the heart. For example, heart sounds may reflect turbulence caused by the closing of heart valves. During a process of "cardiac auscultation," a physician may use a stethoscope to listen to such heart sounds, which may provide information regarding the condition of a patient's heart.

FIG. 1 shows examples of cardiac cycle elements. A healthy adult heart will produce two heart sounds that are often described as a "lub" and a "dub," which occur in sequence during each heartbeat. The "lub" sound corresponds with the first heart sound, also referred to as S1, whereas the "dub" sound corresponds with the second heart sound S2. In addition to the normal S1 and S2 heart sounds, a variety of other sounds may be present including heart murmurs, adventitious sounds, and gallop rhythms S3 and S4.

As indicated in FIG. 1, the S1 heart sound is caused by the closure of the mitral and tricuspid valves, which are collectively referred to as the atrioventricular valves. The S1 heart sound results from reverberation within the blood associated with the sudden blockage of blood flow caused by closing the atrioventricular valves. Both the S1 heart sound and the S2 heart sound may include multiple components. The component of the S1 heart sound that corresponds with closing the mitral valve may be denoted as $M_1$ and the component of the S1 heart sound that corresponds with closing the tricuspid valve may be denoted as $T_1$. $M_1$ normally precedes $T_1$.

As shown in FIG. 1, the S2 heart sound corresponds with the end of ventricular systole and the beginning of ventricular diastole. As the left ventricle empties, the pressure of the left ventricle falls below the pressure in the aorta. Aortic blood flow quickly reverses back toward the left ventricle and is stopped by aortic valve closure. Likewise, as the pressure in the right ventricle falls below the pressure in the pulmonary artery, the pulmonary valve closes.

The S2 heart sound includes an A2 component, which is caused by closing the aortic valve. The S2 heart sound also includes a P2 component, which is caused by closing the pulmonary valve. In general, A2 precedes P2. The aortic valve and the pulmonary valve are collectively referred to as the semilunar valves. The A2 component is caused by closing the aortic valve and the P2 component is caused by closing the pulmonary valve.

Figure 2:
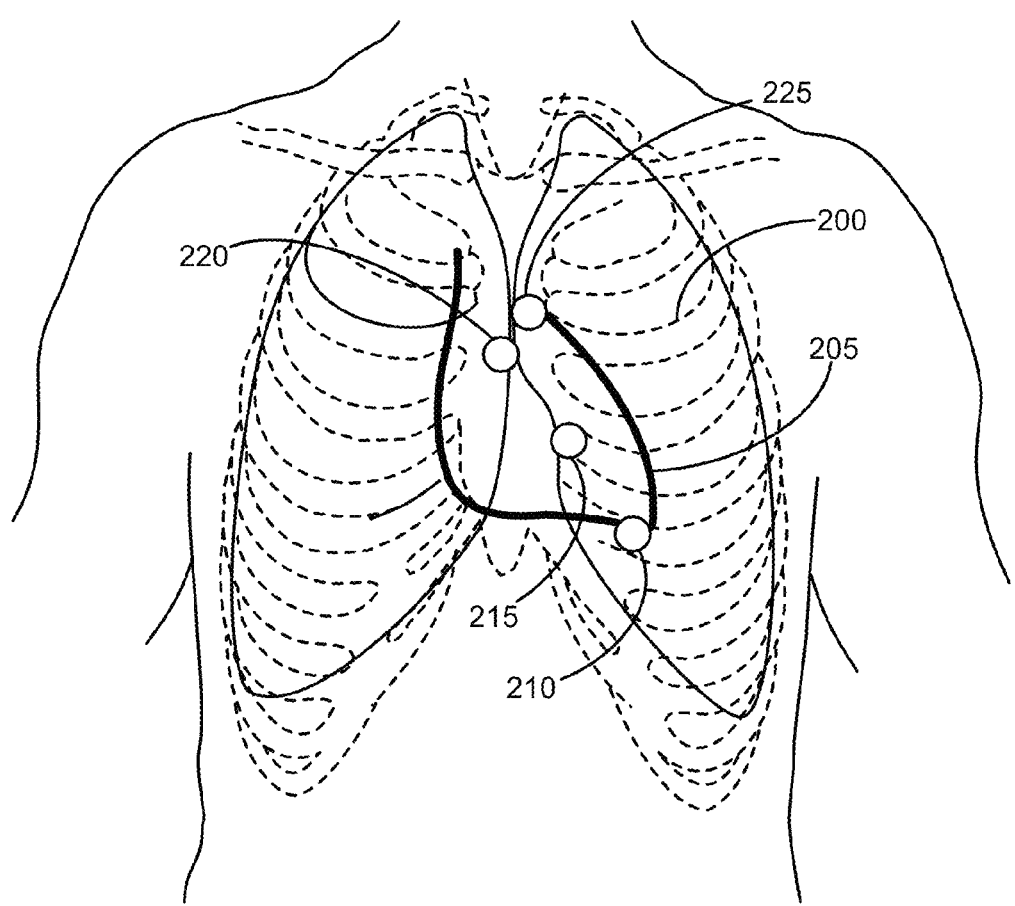
FIG. 2 shows the locations on which a prior art stethoscope should be placed for proper auscultation of the S1 and S2 heart sounds.

FIG. 2 shows the locations on which a prior art stethoscope should be placed for proper auscultation of the S1 and S2 heart sounds. A human ribcage 200 and collar bones are shown by dashed lines and an outline of a human heart 205 is shown via solid black lines. For proper auscultation of S1 heart sounds, a physician should place the stethoscope on auscultation site 210, near the mitral valve, and on auscultation site 215, near the tricuspid valve. For proper auscultation of S2 heart sounds, a physician should place the stethoscope on auscultation site 220, near the aortic valve, and on auscultation site 225, near the pulmonary valve. Aside from the challenges of evaluating the heart sounds, merely placing a stethoscope in the proper locations would be challenging for a typical non-physician.

Figure 3A:
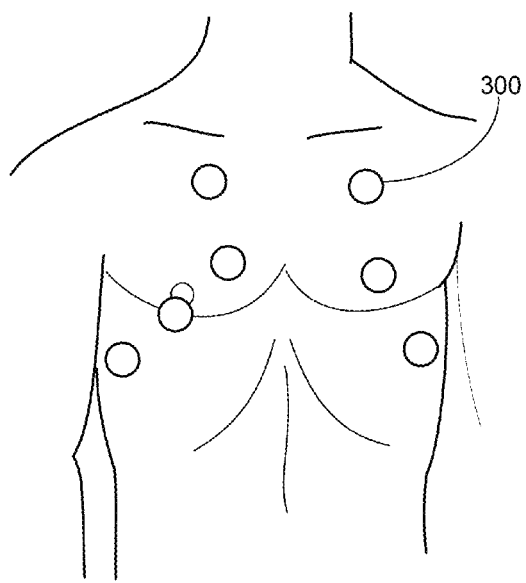
FIGS. 3A and 3B show stethoscope locations for auscultation of breathing sounds.
Figure 3B:
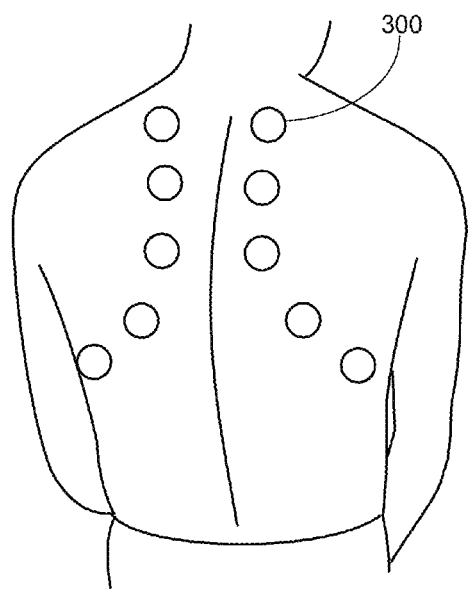

FIGS. 3A and 3B show stethoscope locations for auscultation of breathing sounds. In FIG. 3A, the stethoscope locations 300 are shown on the front of a human chest, whereas in FIG. 3B the stethoscope locations 300 are shown on the back of a human chest. Auscultation of breathing sounds may reveal normal breathing sounds and/or abnormal breathing sounds such as crackles, wheezes, pleural friction rubs (squeaking or grating sounds of the pleural linings rubbing together), etc. A trained physician knows the locations on which the stethoscope should be placed and knows the characteristic properties of normal and abnormal breathing sounds. In addition to the challenges of evaluating the properties of breathing sounds, even placing a stethoscope in the proper locations could be challenging for non-physicians.

Figure 4:
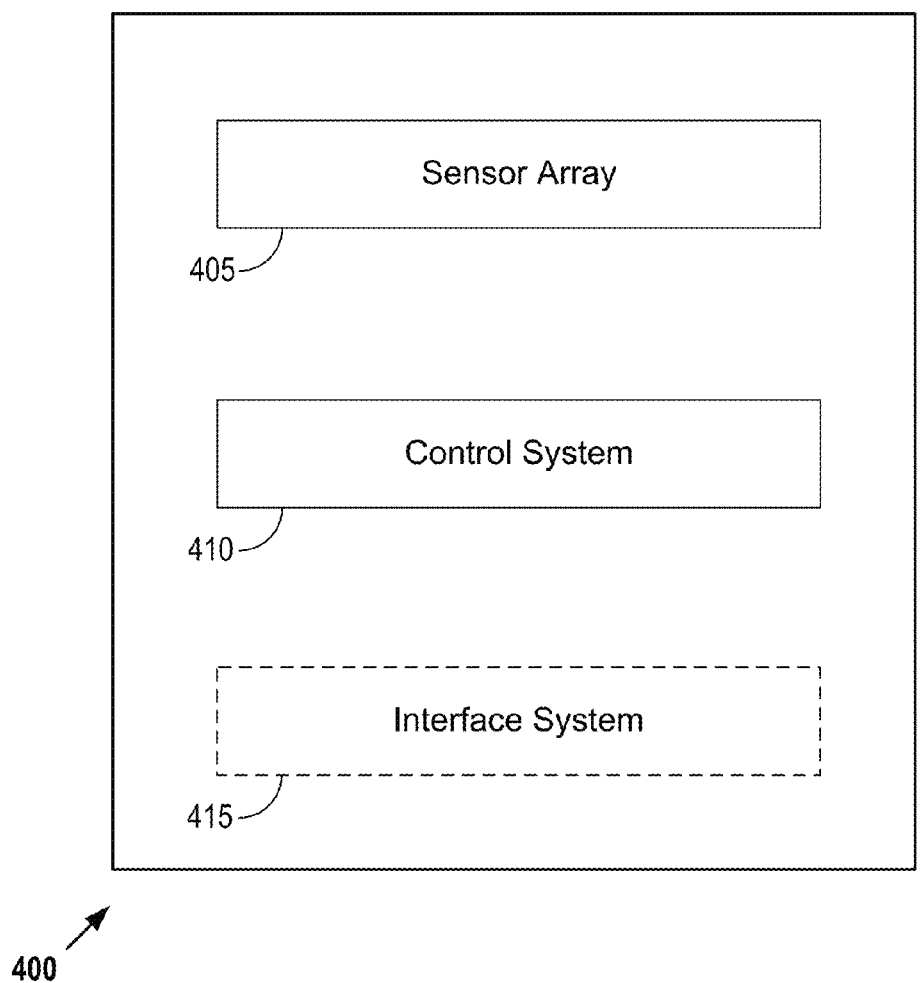
FIG. 4 is a block diagram that shows examples of components of apparatus in which some aspects of the present disclosure may be implemented.

FIG. 4 is a block diagram that shows examples of components of apparatus in which some aspects of the present disclosure may be implemented. As with other implementations disclosed herein, the numbers of elements and types of elements shown in FIG. 4 are merely shown by way of example. Other implementations may have more, fewer or different elements. In the implementation shown in FIG. 4, the stethoscope system 400 includes a sensor array 405 and a control system 410.

The control system 410 may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. The control system 410 may be capable of performing some or all of the methods described herein. In some implementations, the control system 410 may be capable of controlling one or more components of the stethoscope system 400. For example, the control system 410 may be capable of controlling the sensor array 405.

In some implementations, the control system 410 may be capable of controlling the stethoscope system 400 according to instructions (e.g., software) stored on one or more non-transitory media. Such non-transitory media may include one or more memory devices of the stethoscope system 400, which may include one or more random access memory (RAM) devices, one or more read-only memory (ROM) devices, etc. In some implementations, the control system 410 may include one or more of such memory devices. Accordingly, at least some aspects of the subject matter disclosed herein may be implemented via one or more non-transitory media having software stored thereon.

In the example shown in FIG. 4, the stethoscope system 400 includes an optional interface system 415. The interface system 415 may, for example, include a wireless interface system. In some implementations, the interface system 415 may include a network interface, an interface between the control system 410 and a memory system and/or an external device interface (e.g., a port). In some implementations, the stethoscope system 400 may be capable of wireless communication with a second device via the interface system 415. Some examples are described below.

Figure 5A:
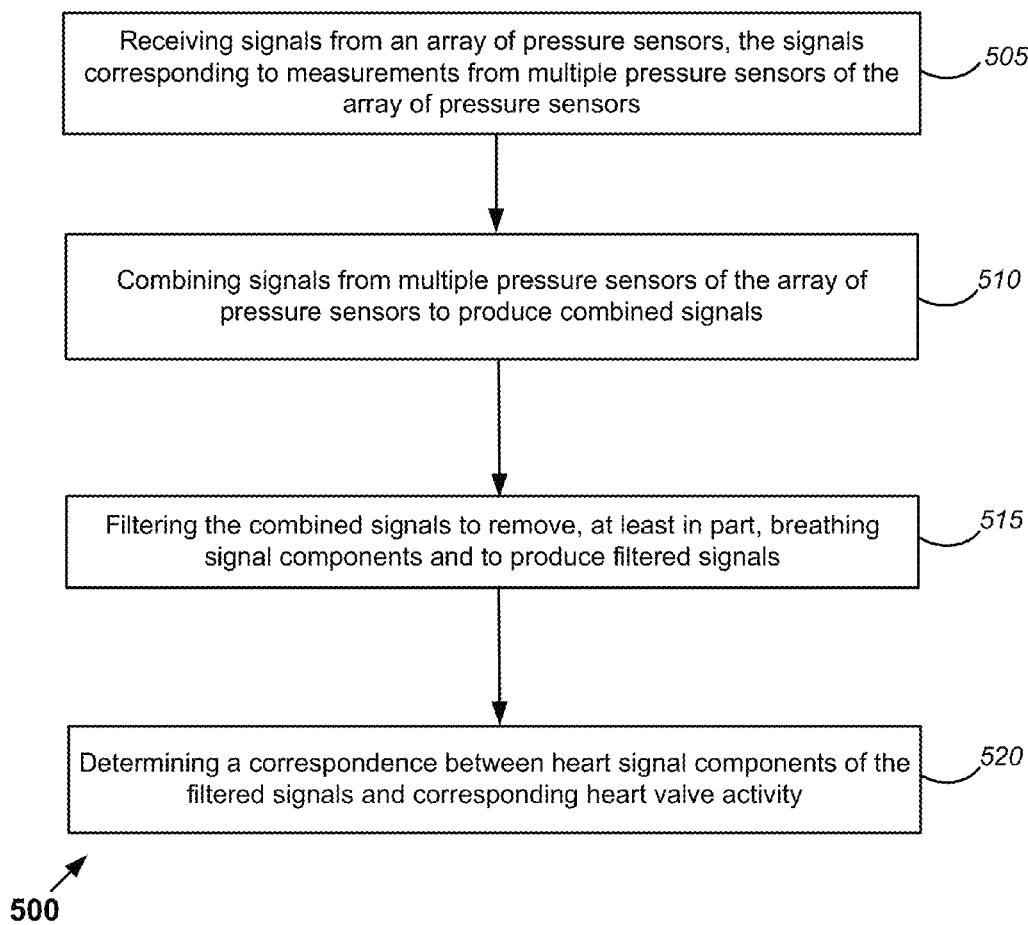
FIG. 5A is a flow diagram that outlines one example of a method for controlling a stethoscope system.

FIG. 5A is a flow diagram that outlines one example of a method for controlling a stethoscope system. The blocks of method 500, like other methods described herein, are not necessarily performed in the order indicated. Moreover, such methods may include more or fewer blocks than shown and/or described. In one example, the method may be implemented by the stethoscope system 400 shown in FIG. 4. The blocks of method 500 may, for example, be performed (at least in part) by a control system such as the control system 410 that is shown in FIG. 4. However, method 500 also may be performed by other devices or systems, such as the stethoscope system 400 shown in FIG. 9 and described below. In some examples, method 500 may be implemented, at least in part, according to software stored on one or more non-transitory media.

In this example, block 505 involves receiving signals from an array of pressure sensors. The signals may, for example, be received by a control system from a sensor array such as the sensor array 405 shown in FIG. 4 or the sensor array 405 shown in FIG. 9. In this example, the signals correspond to measurements from multiple pressure sensors of the array. In some implementations, the signals may correspond to multiple simultaneous, or substantially simultaneous, measurements from multiple pressure sensors of the array. According to some examples, the signals may correspond to multiple simultaneous and redundant measurements from multiple pressure sensors of the array.

According to this example, block 510 involves combining signals from multiple pressure sensors of the array of pressure sensors to produce combined signals. In some examples block 510 (or another block) may involve determining correlations and/or diversity of signals, of signal components, or of both signals and signal components. Various examples are disclosed herein.

Figure 6:
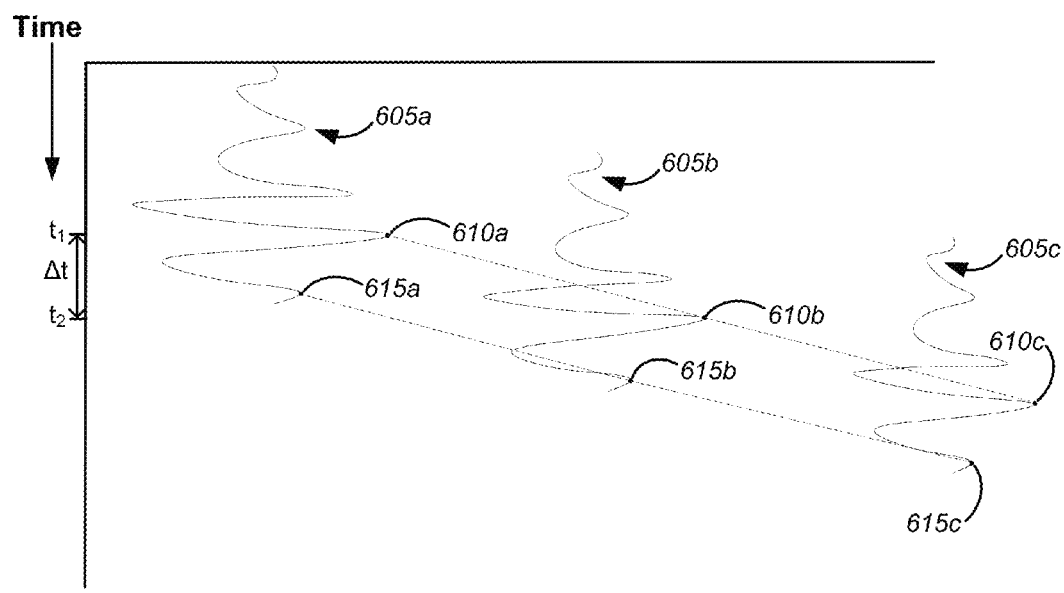
FIG. 6 shows examples of portions of signals from multiple pressure sensors of an array.

FIG. 6 shows examples of portions of signals from multiple pressure sensors of an array. In this example, the signal portions are shown in the time domain. In FIG. 6, the vertical axis indicates time, with time increasing in the downward direction. FIG. 6 shows signal portions 605a, 605b and 605c. It may be seen that the signal portions 605a, 605b and 605c are not identical, in part because they are time-shifted and because their components (for example, their peaks and troughs) have differing amplitudes.

However, it may be seen that the components of the signal portions 605a, 605b and 605c correspond with one another. For example, point 610a of the signal portion 605a corresponds with point 610b of the signal portion 605b and with point 610c of the signal portion 605c. Similarly, point 615a of the signal portion 605a corresponds with point 615b of the signal portion 605b and with point 615c of the signal portion 605c. Because the components of the signal portions 605a, 605b and 605c correspond with one another, the corresponding signals may be referred to herein as "redundant" signals. Accordingly, the term "redundant" as used herein does not necessarily mean "identical."

In this example, point 610a occurs at a time $t_1$ and the point 610b occurs at a time $t_2$. The time difference between the time $t_1$ and the time $t_2$ is $\Delta t$. If $\Delta t$ were added to the time values of the signal portion 605a, or if $\Delta t$ were subtracted from the time values of the signal portion 605b, the peaks and troughs of the signal portions 605a and 605b would correspond more closely in time.

The value of $\Delta t$ may be determined by performing a cross-correlation between functions that correspond with the signal portions 605a and 605b. Accordingly, some examples may involve determining a correlation between signals received from different sensors. For example, block 510 of FIG. 5 (or a pre-processing block that is performed before block 510) may involve determining a cross-correlation $f(t)*g(t)$ between a first function $f(t)$ that corresponds with the signal portion 605a and a second function g(t) that corresponds with the signal portion 605b or the signal portion 605c.

If the functions $f(t)$ and g(t) were identical, differing only by an unknown shift along the time axis, a cross-correlation process may be used to determine by how much g(t) would need be shifted along the time axis to make g(t) identical to $f(t)$. One could envision the mathematical process as sliding the function g(t) along the time axis and calculating the integral of the product of $f(t)$ and g(t) at each position. When the functions match, the value of the cross-correlation $f(t)*g(t)$ is maximized. Even though the signal portions 605a and 605b are not identical, determining the cross-correlation $f(t)*g(t)$ between a first function $f(t)$ that corresponds with the signal portion 605a and a second function g(t) that corresponds with the signal portion 605b would nonetheless allow a determination of the value of $\Delta t$ at which the cross-correlation is maximized.

According to the implementation shown in FIG. 5, block 510 involves combining signals from multiple pressure sensors of the array of pressure sensors, to produce combined signals. Combining signals from multiple pressure sensors, for example by integrating the corresponding values of multiple signals, may attenuate noise and enhance signal values. A process of combining signals from multiple pressure sensors of the array of pressure sensors may, in some implementations, be performed after a cross-correlation and time-shifting process such as that described above. In some examples, the cross-correlation and time-shifting processes may be part of a pre-processing block that is performed before block 510.

According to some implementations, method 500 may involve transforming the signals from a time domain into a frequency domain, e.g., via some type of Fourier transform. According to some such implementations, the signals may be transformed from a time domain into a frequency domain prior to block 515. In some examples, the Fourier transform may be a Discrete Fourier Transform (DFT), such as a Fast Fourier Transform (FFT). Some implementations may involve implementing a Wigner distribution function. Alternatively, or additionally, method 500 may involve a wavelet transform, such as a continuous wavelet transform or a discrete wavelet transform.

In the implementation of FIG. 5, block 515 involves filtering the combined signals to remove, at least in part, the breathing signal components. In some examples, block 515 may involve applying one or more filters in the frequency domain. For example, a control system may apply one or more filter functions, or filter transfer functions, to the output of a Fourier transform of the input signals. The filter functions may include one or more low-pass filters, high-pass filters, Gaussian filters, Butterworth filters and/or other filters. The filtering process(es) of block 515 may take into account known properties of heart signal components and breathing signal components, such as those discussed below.

In this example, block 520 involves determining a correspondence between heart signal components of the filtered signals and corresponding heart valve activity. In some such examples, block 520 may involve determining a correspondence between heart signal components of the filtered signals and corresponding semilunar valve activity (e.g., aortic valve and/or pulmonary valve activity), corresponding mitral valve activity, corresponding tricuspid valve activity, etc. Some implementations may involve determining a correspondence between heart signal components of the filtered signals and corresponding parts of a cardiac cycle. Some such implementations may involve identifying S1 heart sounds, identifying S2 heart sounds, or identifying both S1 and S2 heart sounds. Alternatively, or additionally, some implementations may involve identifying S3 heart sounds, S4 heart sounds or both S3 heart sounds and S4 heart sounds.

Figure 5B:
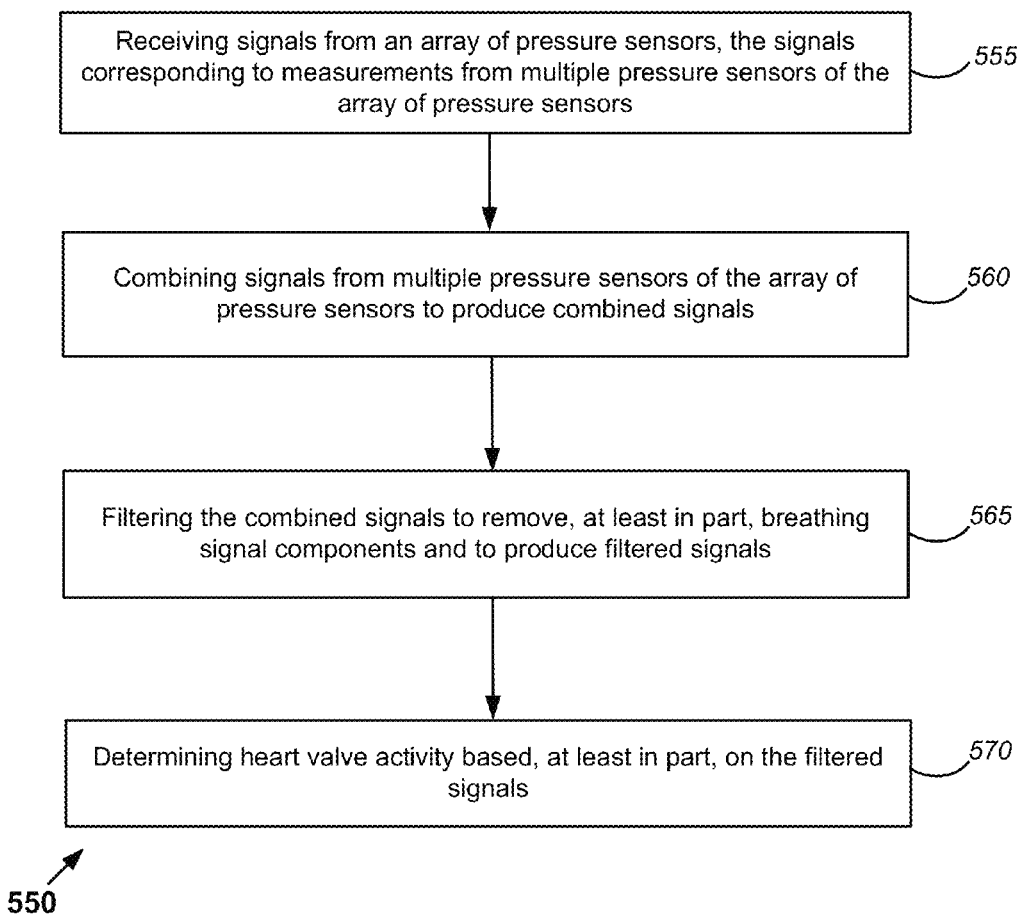
FIG. 5B is a flow diagram that outlines another example of a method for controlling a stethoscope system.

FIG. 5B is a flow diagram that outlines another example of a method for controlling a stethoscope system. The blocks of method 550, like other methods described herein, are not necessarily performed in the order indicated. Moreover, such methods may include more or fewer blocks than shown and/or described. In one example, the method may be implemented by the stethoscope system 400 shown in FIG. 4. The blocks of method 550 may, for example, be performed (at least in part) by a control system such as the control system 410 that is shown in FIG. 4. However, method 550 also may be performed by other devices or systems, such as the stethoscope system 400 shown in FIG. 9 and described below. In some examples, method 550 may be implemented, at least in part, according to software stored on one or more non-transitory media.

In this example, blocks 555-565 may be performed substantially as blocks 505-515 are performed. However, in this example block 570 involves determining heart valve activity based, at least in part, on the filtered signals. Block 570 may, for example, involve determining semilunar valve activity (e.g., aortic valve and/or pulmonary valve activity), determining mitral valve activity and/or determining tricuspid valve activity, etc. Accordingly, while the operation(s) of block 570 may be similar to those of block 520, block 570 does not necessarily involve determining a correspondence between heart signal components of the filtered signals and corresponding heart valve activity.

Figure 7:
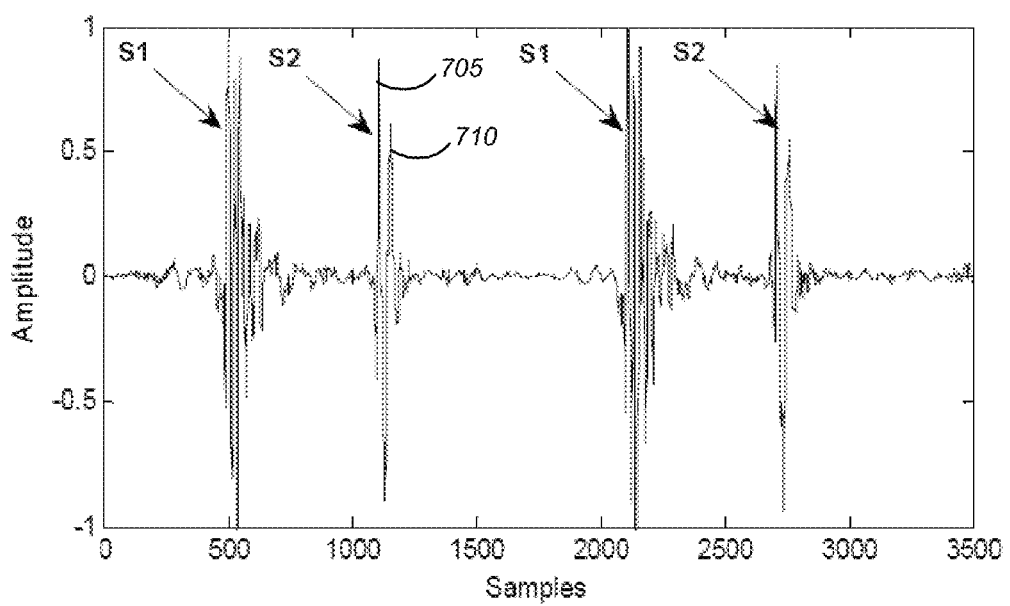
FIG. 7 shows examples of S1 and S2 heart sounds in the time domain.

FIG. 7 shows examples of S1 and S2 heart sounds in the time domain. FIG. 7 originally appeared in Zhidong, Zhao, Shen, Qinqin and Ren, Fangqin, *Heart Sound Biometric System Based on Marginal Spectrum Analysis* in Sensors, Volume 13, Issue 2 (MDPI—Open Access Publishing 2013) and may be reproduced for noncommercial or commercial purposes pursuant to the terms of the Creative Commons Attribution 3.0 Unported License (CC BY 3.0). It may be seen in FIG. 7 that both the time duration and the amplitude of S1 heart sounds tend to be greater than those of S2 heart sounds. Therefore, some implementations may involve evaluating the time duration, the amplitude or both the time duration and the amplitude of signals received from the sensor array. In the examples shown in FIGS. 5A and 5B, method 500 and/or method 550 may involve evaluating the time duration, the amplitude or both the time duration and the amplitude of filtered signals, received after the filtering process of block 515 or block 565. If the filtering process is performed after a transform into the frequency domain, a wavenumber domain, etc., such evaluations may be made after a subsequent inverse transform back to the time domain.

According to some implementations, method 500 and/or method 550 may involve identifying the components of S1 heart sounds, identifying the components of S2 heart sounds, or identifying the components of both S1 and S2 heart sounds. For example, block 520 may involve determining the aortic component or "A2" and the pulmonic component or "P2" of S2 heart sounds. The A2 component of a healthy person's heart normally precedes the P2 component, as shown in FIG. 7: here, the A2 component 705 precedes the P2 component 710. The time difference between A2 and P2 should generally be greater during inspiration than during expiration. Moreover, the A2 component 705 generally includes higher-amplitude signals than those of the P2 component 710, as shown in FIG. 7. Therefore, in some implementations block 520 may involve evaluating the temporal characteristics (such as the time difference between A2 and P2) and the frequency spectrum of heart signal components.

In some implementations method 500 and/or method 550 may involve evaluating the frequency spectrum of heart signal components. FIG. 8A shows an example of a frequency spectrum for S1 heart sounds. FIG. 8B shows an example of a frequency spectrum for S2 heart sounds. FIGS. 8A and 8B originally appeared in Debbal, S. M., *Computerized Heart Sounds Analysis* (InTech September 2011) ("Debbal"), and may be reproduced for noncommercial or commercial purposes pursuant to the terms of the Creative Commons Attribution 3.0 Unported License (CC BY 3.0).

Referring first to FIG. 8A, it may be seen that according to Debbal, the highest amplitudes for S1 heart sounds occur between 50 and 130 Hz. FIG. 8B indicates that Debbal found that the highest amplitudes for S2 heart sounds occur between 75 and 200 Hz. Moreover, it may be seen from FIG. 8B that the A2 component of a healthy person's heart generally includes higher-frequency signals than those of the P2 component. In this example, the peak amplitude for the P2 component occurs at slightly less than 100 Hz, whereas the peak amplitude for the A2 component occurs at approximately 160 Hz. However, other authors have concluded that the major concentrations of energy for S2 heart sounds occurs below 150 Hz. (See, e.g., Arnott, P. J., et al, *Spectral Analysis of Heart and Breath sounds* (J Biomed Eng. 1984 Apr.; 6(2): 121-8) ("Arnott").)

Arnott also determined that the highest detected amplitudes for breathing sounds are different, depending on where the breathing sounds are measured. For example, the peak amplitudes for breathing sounds that were measured over the base of the right lung were at 446 Hz for inspiratory breathing sounds, with a standard deviation of +/−143 Hz, and at 286 Hz for expiratory breathing sounds, with a standard deviation of +/−53. (Id: see Abstract.) According to Arnott, the highest detected amplitudes for breathing sounds that were measured over the base of the left lung were at 475 Hz for inspiratory breathing sounds, with a standard deviation of +/−115, and at 284 Hz for expiratory breathing sounds, with a standard deviation of +/−47. (Id.) Arnott indicates that the highest detected amplitudes for breathing sounds measured over the interscapular region were at 434 Hz for inspiratory breathing sounds, with a standard deviation of +/−130 Hz, and at 338 Hz for expiratory breathing sounds, with a standard deviation of +/−77. (Id.) Per Arnott, the highest detected amplitudes for breathing sounds measured over the over the right anterior chest were at 604 Hz for inspiratory breathing sounds, with a standard deviation of +/−302, and at 406 Hz for expiratory breathing sounds, with a standard deviation of +/−205. (Id.)

It may be determined from the foregoing that if sensor data are obtained for a sequence of inspiratory breathing sounds and expiratory breathing sounds, inspiratory breathing sounds and expiratory breathing sounds may be distinguished according to the frequency spectra of the breathing sounds: the breathing sounds that include more energy in a relatively higher frequency range will generally correspond to inspiratory breathing sounds.

Accordingly, some implementations may involve identifying inspiratory breathing sounds and expiratory breathing sounds according to a spectral analysis. In some examples, the spectral analysis may be part of the analysis of block 510 of FIG. 5. In such examples, method 500 and/or method 550 may involve not only distinguishing breathing signal components from heart signal components, but also may involve determining characteristics of the breathing signal components.

According to some such implementations, a control system may be capable of transforming signals from an array of pressure sensors from the time domain into the frequency domain. The control system may be capable of identifying inspiratory breathing sounds and expiratory breathing sounds according to a spectral analysis. In some such examples, the control system may be capable of identifying time intervals corresponding to inspiratory breathing sounds and time intervals corresponding to expiratory breathing sounds. The control system also may be capable of distinguishing breathing signal components from heart signal components.

In some implementations, block 515 of FIG. 5A and/or block 565 of FIG. 5B may involve one or more filtering processes that take into account the characteristics of the frequency spectra of heart signal components and breathing signal components. According to some such implementations, block 515 and/or block 565 may involve applying one or more filters in the frequency domain that are selected to pass most of the energy for signals corresponding to S1 and S2 heart sounds, while attenuating most of the energy for signals corresponding to breathing sounds. Alternatively, or additionally, some implementations may involve applying one or more filters in the frequency domain that are selected to pass most of the energy for signals corresponding to breathing sounds, while attenuating most of the energy for signals corresponding to S1 and S2 heart sounds. For example, a control system may apply one or more filter functions, or filter transfer functions, to the output of a Fourier transform of the input signals. The filter functions may include one or more low-pass filters, high-pass filters, Gaussian filters, Butterworth filters and/or other filters.

In some implementations, the control system may be capable of applying a low-pass filter with a roll-off that starts at approximately 200 Hz, e.g. at 190 Hz, 195 Hz, 200 Hz, 205 Hz, 210 Hz, 215 Hz, etc. Such implementations may significantly attenuate signals having frequencies that are greater than approximately 200 Hz. In some implementations, the control system may be capable of applying a band-pass filter that passes a frequency range between about 50 and 200 Hz., e.g., between 55 and 200 Hz., between 55 and 205 Hz., between 55 and 210 Hz., between 60 and 200 Hz., between 60 and 205 Hz., between 60 and 210 Hz., between 65 and 200 Hz., etc. Such low-pass and band-pass filters may pass most of the energy for signals corresponding to S1 and S2 heart sounds, while attenuating most of the energy for signals corresponding to breathing sounds. After filtering in the frequency domain, some implementations may involve applying an inverse transform to the filtered signals in the frequency domain to produce filtered signals in the time domain.

Some implementations may involve at least some analysis and/or processing in the time domain. Some post-filtering examples are described above with reference to FIG. 7, in which method 500 of FIG. 5A and/or method 550 of block FIG. 5B may involve evaluating the time duration, the amplitude or both the time duration and the amplitude of filtered signals, received after the filtering process of block 515 or block 565. If the filtering process is performed after a transform into the frequency domain, a wavenumber domain, etc., such evaluations may be made after a subsequent inverse transform back to the time domain. However, in some implementations, at least some analysis and/or processing may be performed in the time domain before the filtering process of block 515 or block 565. According to some examples, this time domain analysis may be part of block 510, or may be part of a separate process that occurs before block 515 or block 565.

For example, FIG. 7 indicates that both the time duration and the amplitude of S1 heart sounds tend to be greater than those of S2 heart sounds. Therefore, some implementations may involve evaluating the time duration, the amplitude or both the time duration and the amplitude of signals received from the sensor array. Some such examples may involve evaluating the time duration, the amplitude or both the time duration and the amplitude of filtered signals prior to the filtering process of block 515 or block 565.

According to some such implementations, signals corresponding to S1 heart sounds and signals corresponding to S2 heart sounds may be identified, segregated and transformed into the frequency domain prior to the filtering process of block 515 or block 565. In some such implementations, the one or more filters that are applied to signals corresponding to S1 heart sounds in one or more filters that are applied to may be different from the one or more filters that are applied to S2 heart sounds. For example, block 515 or block 565 may involve applying a low-pass filter or a band-pass filter with a roll-off that starts at approximately 150 Hz to signals corresponding to S1 heart sounds, e.g. a roll-off that starts at 125 Hz, 130 Hz, 140 Hz, 145 Hz, 150 Hz, 155 Hz, etc. Block 515 or block 565 may involve applying a low-pass filter or a band-pass filter with a roll-off that starts at approximately 200 Hz to signals corresponding to S2 heart sounds, e.g. a roll-off that starts at 190 Hz, 195 Hz, 200 Hz, 205 Hz, 210 Hz, 215 Hz, etc. Such implementations have the potential advantage of retaining most of the energy corresponding to the S1 and S2 heart sounds, while attenuating energy corresponding to noise or to breathing sounds.

FIG. 9 shows an example of a stethoscope system. In this example, the stethoscope system 400 includes a patch 901 that includes a sensor array 405. Here, the sensor array 405 is a two-dimensional array of pressure sensors 905 having 3 rows and 4 columns. Accordingly, FIG. 9 shows an example of an M by N array of pressure sensors, wherein M and N are integers. In this example, M equals 3 and N equals 4. In this implementation, the pressure sensors 905 of the sensor array 405 are substantially identical pressure sensors. For example, the pressure sensors 905 may have identical specifications and may actually be identical, within a range of manufacturing tolerances.

Alternative implementations may include other types of sensors, other configurations of sensors, a different number of sensors, etc. For example, in some implementations the sensor array 405 may include an M by M array of pressure sensors. In some implementations the sensor array 405 may include a non-rectangular array of pressure sensors, such as an oval array, a circular array, etc. In some implementations, the sensor array 405 may be substantially rectangular, but may include one or more rows or columns that are relatively longer or shorter than the other rows or columns. For example, some such implementations may include one or more rows having additional pressure sensors, such as the second row of the sensor array 405 shown in FIG. 9 that includes optional sensors 905a and 905b. In other examples, the pressure sensors 905 of the sensor array 405 may be similar pressure sensors, but all of the pressure sensors 905 may not be identical, or substantially identical, pressure sensors. In some implementations, the patch 901 may be included in a sleeve, in a wrap or in another type of clothing or accessory. In other implementations, the patch 901 may be embedded in furniture, in a medical probe, etc.

As shown in FIG. 9, the sensor array 405 may, in some examples, occupy a substantial portion of a patient's chest 907. In some such examples, the signals obtained by sensors of the sensor array 405 may correspond to multiple simultaneous measurements of different areas of the patient's chest. For example, the signals may correspond to multiple simultaneous measurements of vibrations produced by one heart valve or multiple simultaneous measurements of vibrations produced by two or more heart valves.

In this example, the sensors 905 of the sensor array 405 are mounted in backing material 910, which may include any suitable material. In this example, the patch 901 includes backing material 910, which is flexible and may easily be conformed to a human chest. In some implementations, the backing material may include an elastic membrane and the pressure sensors 905 may be arranged on or embedded within the elastic membrane. The sensors 905 may be rigid or flexible, depending on the particular implementation. In some implementations, the backing material may include a woven material and the pressure sensors 905 may be woven into the woven material. In some embodiments, the backing material may include a non-woven material and the pressure sensors 905 may be arranged on or embedded within the non-woven material. According to some implementations, the backing material 910 includes at least one layer of adhesive material for secure placement on a patient's body. In some implementations of the sensor array 405, the backing material 910 may include multiple layers of adhesive material. In some such implementations, the layers of adhesive material may be separated from one another, for example by peeling one layer of adhesive material from another layer. In some such examples, each of the layers of adhesive material may adhere more strongly to a patient's skin than to adjacent adhesive layers. Some such implementations may allow the sensor array 405 to be used multiple times for a patient, or for multiple patients, with a clean adhesive layer provided against the patient's chest each time.

In this example, the control unit 915 includes a control system and an interface system. The control system may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. In some implementations, the control system may be capable of controlling one or more components of the stethoscope system 400. For example, the control system may be capable of controlling the sensor array 405. The control unit may be flexible or rigid, depending on the particular implementation.

Accordingly, the control unit 915 may be capable of providing the functionality of the control system 410 and the interface system 415 that are shown in FIG. 4 and described elsewhere herein. For example, the control unit 915 may be capable of providing the functionality described above with reference to the blocks of FIG. 5A and/or FIG. 5B. In some implementations, the control unit 915 may be capable of providing the additional functionality that is described above with reference to FIGS. 6-8.

In some implementations, the control system of the control unit 915 may include one or more memory devices, such as one or more random access memory (RAM) devices, one or more read-only memory (ROM) devices, or other non-transitory media. Accordingly, at least some aspects of the subject matter disclosed herein may be implemented via one or more non-transitory media having software stored thereon, via firmware, etc.

In some implementations, the control unit 915 may be capable of providing additional functionality. For example, in some implementations, the control unit 915 may be capable of performing additional signal pre-processing. In some implementations that are described above, a pre-processing block may be performed before block 510 of FIG. 5A or before block 560 of FIG. 5B. In some examples, the pre-processing block may involve cross-correlation and time-shifting processes. According to some implementations, the control unit 915 may be capable of performing additional signal pre-processing, such as identifying noisy or "dead" sensors and deleting the signals from such sensors. In some implementations, the control unit 915 may be capable of normalizing the amplitudes of signals received from multiple pressure sensors of the sensor array 405.

In some implementations, the interface system of the control unit 915 may include a network interface, an interface between the control system and a memory system and/or an external device interface (e.g., a port). In this example, the interface system is capable of wireless communication with one or more other devices. In the implementation shown in FIG. 9, the interface system is capable of wireless communication with a second device, which is a mobile device 920 in this example.

In some implementations, at least a portion of the control system functionality that is described herein may be performed by a second device, such as the mobile device 920. Accordingly, the control system 410 that is disclosed herein may be disposed, at least in part, in one or more other devices. According to some implementations, the control system of the control unit 915 may be capable of receiving instructions from a second device, via the interface system, and of controlling at least a portion of the stethoscope system 400 according to the instructions. However, in some examples the instructions may originate from another device, which may or may not be in the vicinity of the stethoscope system 400. Some examples are described below with reference to FIG. 11.

In some implementations, the control system of the control unit 915 (and/or the control system of the mobile device 920) may be capable of encrypting data, e.g., before transmitting the data via an interface system. According to some examples, the control system may be capable of encrypting data via symmetric-key cryptography. In some such examples, the control system may be capable of encrypting data via a block cipher cryptographic method, e.g., according to the Data Encryption Standard (DES) or the Advanced Encryption Standard (AES). In some implementations, the control system may be capable of encrypting data via a cryptographic hash function, such as one of the Secure Hash Algorithm (SHA) series of functions, e.g., the SHA-1, the SHA-2 or the SHA-3 algorithm. According to some examples, the control system may be capable of encrypting data via asymmetric-key cryptography methods, such as public-key cryptography methods.

Although the example shown in FIG. 9 shows a stethoscope system 400 that occupies a substantial portion of the patient's chest 907, some implementations of the stethoscope system 400 may not be large enough to cover a particular patient's chest. In some instances, either because of the size of the stethoscope system 400, the size of the patient, or both, it may be difficult to position the stethoscope system 400 in an optimal manner.

Figure 10:
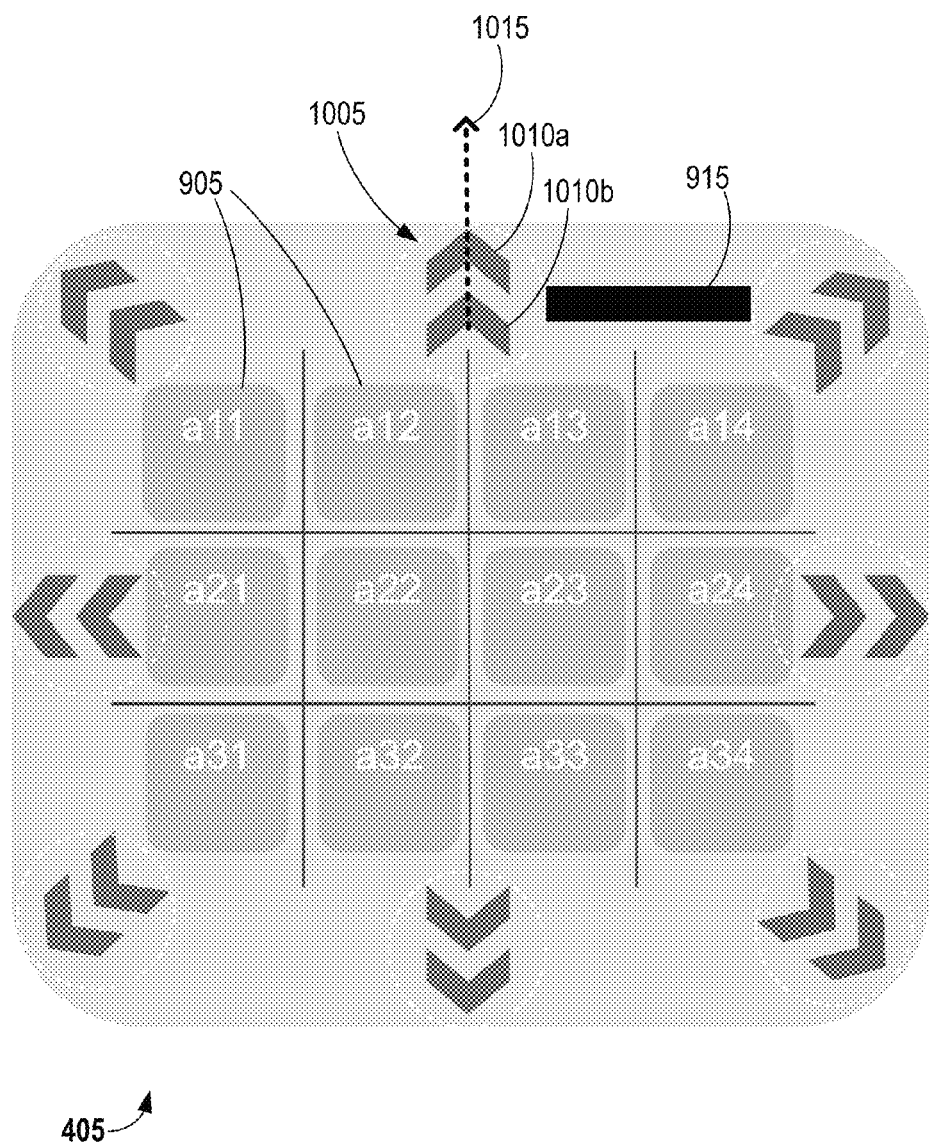
FIG. 10 shows an example of a stethoscope system that includes a user feedback system.

FIG. 10 shows an example of a stethoscope system that includes a user feedback system. Such a user feedback system may, for example, be advantageous for providing feedback to a user regarding proper placement of the stethoscope system 400 on a patient's chest. In this example, the user feedback system of the stethoscope system 400 includes multiple force feedback elements 1005. The numbers, types and orientations of the force feedback elements 1005 that are shown in FIG. 10 are merely examples. Other implementations may include more, fewer and/or different types of force feedback elements 1005. Some implementations of the stethoscope system 400 may not include any of the force feedback elements 1005.

In some implementations, the force feedback elements 1005 may include piezoionic devices. For example, in some implementations the force feedback elements 1005 may include flexible piezoionic devices such as those described in M. S. Sarwar et al., "Transparent and Conformal 'Piezoionic' Touch Sensor," Proceedings of SPIE, 9430 943026-1-943026-9 (2015), which is hereby incorporated by reference. In some implementations, both the force feedback elements 1005 and the pressure sensors 905 may be piezoionic devices. In some such examples, the force feedback elements may be instances of the pressure sensors.

According to some examples, the control system of the control unit 915 (or another control system) may be capable of determining a quality metric for heart signal components, e.g., S1 heart sounds and S2 heart sounds, obtained using the method of 500 from sensor signals and of determining whether the quality metric is less than a quality metric threshold. The quality metric may, in some instances, correspond (at least in part) with a position of the stethoscope system 400.

As noted above, the A2 component of S2 heart sounds generally has higher-amplitude signals than those of the P2 component of S2 heart sounds. Accordingly, in some instances the A2 component may be readily detectable at all of the auscultation sites of a patient's chest (and possibly at other locations of a patient's chest), whereas the P2 component may not be readily detectable at locations that are not near auscultation site 225, near the pulmonary valve (see FIG. 2).

Accordingly, in some examples, the amplitude of the P2 component may be at least one aspect of a quality metric that is determined by the control system of the control unit 915 (or another control system). A quality metric that corresponds to the amplitude of the P2 component may be measured in various ways, depending on the particular implementation. According to some such examples, the quality metric may be determined according to a measured amplitude of the P2 component itself, e.g., according to whether the measured amplitude of the P2 component is above a threshold value. This threshold value is one example of a "quality metric threshold." Alternatively, or additionally, the quality metric may be determined according to a relative amplitude of the A2 and P2 components. For example, the quality metric may be based, at least in part, on the ratio of the amplitude of the P2 component to the amplitude of the A2 component. In other implementations, the quality metric may be based, at least in part, on factors other than the amplitude of the P2 component, for example on the spectral content of the obtained S1 and S2 heart sounds in reference to that expected from typical heart sounds, e.g., as shown in FIGS. 7 and 8.

If the control system of the control unit 915 determines that the quality metric is not at or above a quality metric threshold, in some implementations the control system of the control unit 915 may be capable of providing instructions via the user feedback system. In some implementations, the control system may be capable of controlling one or more of the force feedback elements 1005 to provide user feedback indicating that the stethoscope system 400 should be re-positioned.

For example, the control system of the control unit 915 may determine that the quality metric is not at or above a quality metric threshold and that the pressure sensors a12 and a13 are indicating the highest values of the quality metric, such as the highest-amplitude signals for the P2 component. Alternatively, or additionally, the control system of the control unit 915 may be capable of determining a quality metric gradient. In some such examples, the control system of the control unit 915 may control the force feedback sub-element 1010a, the force feedback sub-element 1010b, or both the force feedback sub-element 1010a and the force feedback sub-element 1010b, to provide force feedback indicating that the stethoscope system 400 should be moved in the direction of the arrow 1015. According to some such implementations, if the control system of the control unit 915 only activates one of the force feedback sub-elements, this indicates that the stethoscope system 400 should be moved a relatively smaller distance than if the control system of the control unit 915 activates both the force feedback sub-element 1010a and the force feedback sub-element 1010b. Alternatively, or additionally, the control system of the control unit 915 may be capable of determining a quality metric gradient and of providing instructions via the user feedback system according to the quality metric gradient.

Some implementations may involve determining other types of quality metrics. In some examples, a quality metric may be based on characteristics of one or more pulses that correspond with heart activity. The pulse characteristics may, for example, include pulse length, pulse shape and/or pulse rate. Pulse shape can be relative to other values, such as amplitude values. There are several classification systems for pulse shapes. In some such classification systems, the dicrotic notch of the arterial pulse wave is regarded as a key factor of pulse shapes. The presence or absence of the dicrotic notch may, for example, be an indication of arterial stiffness.

Accordingly, the determination of such quality metrics may or may not trigger a user prompt for moving the patch 901, depending on the particular implementation. In some implementations, determining such quality metrics may trigger a change in processing of signals received by the patch 901. For example, if a dicrotic notch had previously been detected in a patient's arterial pulse wave but the current arterial pulse waves, after processing, were not indicating a notch, in some implementations of method 500 or method 550, the combined signals of may be processed with a filter that allows more high-frequency signal components to be included in the filtered signals.

According to some implementations, the control system of the control unit 915 (or another control system disclosed herein) may be capable of detecting an abnormality of heart valve activity. According to some such implementations, the control system may be capable of transmitting a signal, via an interface system (such as the interface system 415 of FIG. 4), corresponding to the abnormality. For example, the A2 component of a healthy person's heart normally precedes the P2 component, as shown in FIG. 7. In some implementations, if the control system determines that the P2 component precedes the A2 component, the control system may be capable of transmitting a signal corresponding to the abnormality. As described above, the A2 component generally includes higher-amplitude signals than those of the P2 component. According to some examples, if the control system determines that the P2 component includes higher-amplitude signals than those of the A2 component, the control system may be capable of transmitting a signal corresponding to the abnormality.

The signal corresponding to the abnormality may or may not indicate the type of abnormality, depending on the particular implementation. In some implementations, the control system may be capable of transmitting a signal corresponding to the abnormality via a wireless interface to one or more other devices on a network, which may be a network such as that described below with reference to FIG. 11. The other device(s) may be used by a health care professional, a family member, etc. In some examples, the control system may be capable of transmitting a signal corresponding to the abnormality to a mobile device, such as the mobile device 920a that is shown in FIG. 9. In some implementations, the mobile device may be capable of relaying the signal to another device. In some such implementations, the mobile device may be capable of providing an audio and/or visual alert corresponding to the abnormality.

Figure 11:
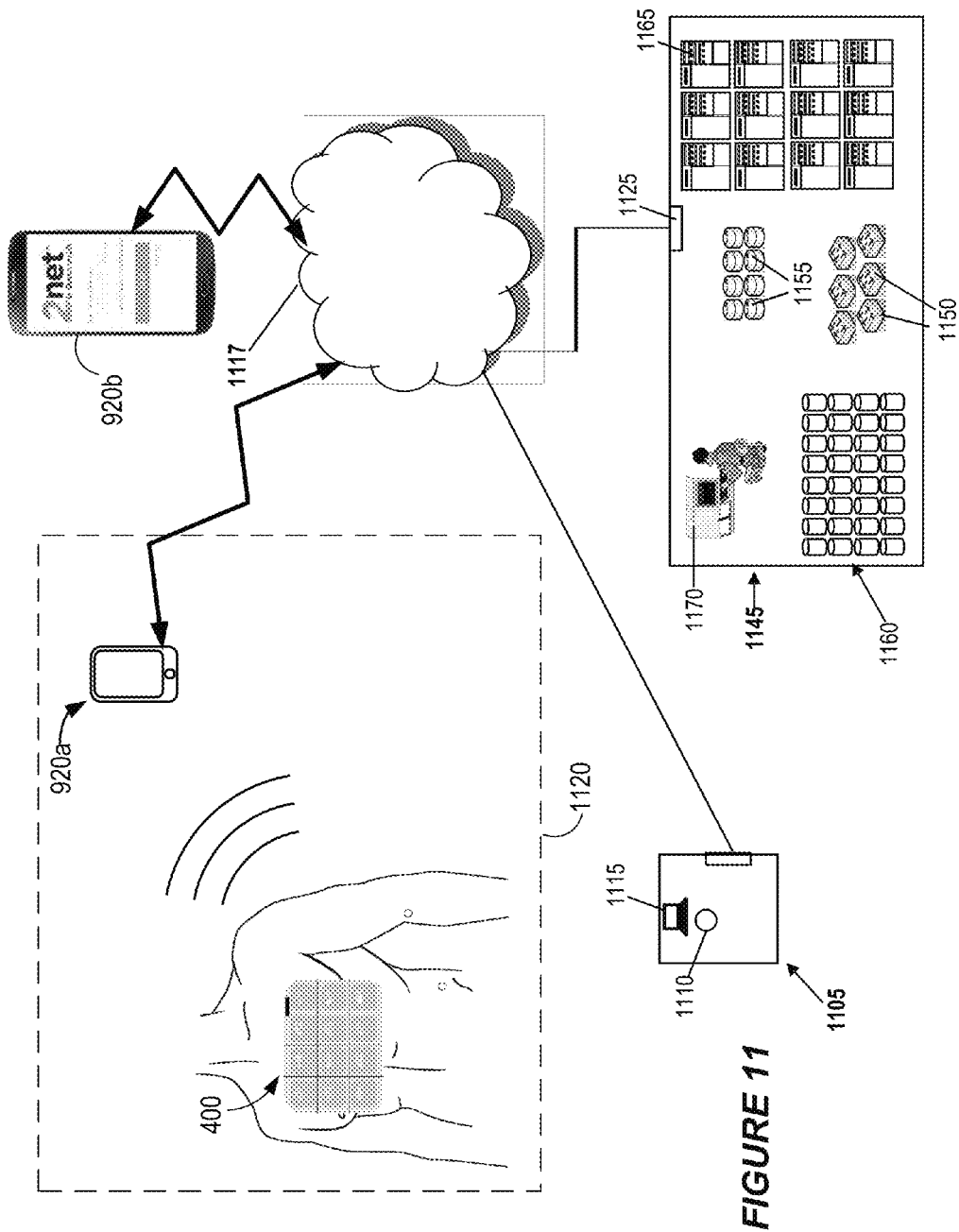
FIG. 11 is a network diagram that shows examples of components of a system in which some aspects of the present disclosure may be implemented.

FIG. 11 is a network diagram that shows examples of components of a system in which some aspects of the present disclosure may be implemented. The numbers, types and arrangements of devices shown in FIG. 11 are merely shown by way of example. In this example, various devices are capable of communication via one or more networks 1117. The networks 1117 may, for example, include the public switched telephone network (PSTN), including cellular telephone networks, the Internet, etc. The mobile devices 920a and 920b shown in FIG. 11 may, for example, include personal computing devices such as smart phones, cellular telephones, tablet devices, etc.

At location 1120, a mobile device 920a is capable of wireless communication with the stethoscope system 400. The mobile device 920a is one example of a "second device" referenced in the foregoing discussion. The mobile device 920a may, for example, be capable of executing software to perform some of the methods described herein, such as receiving data, decrypting data, displaying images corresponding with received data, receiving user input and sending control signals to the stethoscope system 400, etc.

In this example, a data center 1145 includes various devices that may be capable of providing health information services via the networks 1117. Accordingly, the data center 1145 is capable of communication with the networks 1117 via the gateway 1125. Switches 1150 and routers 1155 may be capable of providing network connectivity for devices of the data center 1145, including storage devices 1160, servers 1165 and workstations 1170. Although only one data center 1145 is shown in FIG. 11, some implementations may include multiple data centers 1145.

One or more types of devices in the data center 1145 (or elsewhere) may be capable of executing middleware, e.g., for data management and/or device communication. Health-related information, including but not limited to information obtained by networked stethoscope systems 400, may be uploaded (e.g., from mobile devices such as mobile device 920a) and stored on storage devices 1160 and/or servers 1165. Health-related software also may be stored on storage devices 1160 and/or servers 1165. In some implementations, some such health-related software may be available as "apps" and downloadable by authorized users. Some such apps may be executable on devices that are capable of communication with stethoscope systems 400, such as the mobile device 920a.

In this example, various people and/or entities, including but not limited to health care professionals, patients, patients' families, insurance company representatives, etc., may obtain information regarding, or obtained by, stethoscope systems 400. The information may include, but may not be limited to, data obtained by one or more stethoscope systems 400, other sensor data (such as temperature data) obtained by one or more stethoscope systems 400, etc.

In some examples, authorized people and/or entities may obtain such information via the data center 1145. Alternatively, at least some people and/or entities may be authorized to obtain such information via a data feed from stethoscope systems 400, e.g., via corresponding devices that are in communication with the stethoscope systems 400. Accordingly, in some examples one or more other devices (such as mobile devices 920 or devices of the data center 1145) may act as intermediaries for such data feeds. Such devices may, for example, be capable of applying data encoding algorithms, data compression algorithms, data encryption algorithms, data filtering algorithms, executing data summary and/or analysis software, etc. In some implementations, data encoding algorithms, data decoding algorithms, data compression algorithms, data encryption and decryption algorithms, data filtering, summary software, analysis software, etc., may be available as "apps" and downloadable (e.g., from the data center 1145) by authorized users.

In this example, a family member of an authorized user is logging into the system, via the mobile device 920b, in order to access physiological data obtained by the stethoscope system 400 from the user in location 1120. FIG. 11 also depicts a doctor's office 1105, from which a health care professional 1110 is using a laptop 1115 to access information from the data center 1145. The information may include information obtained by the stethoscope system 400 in location 1120 and/or information obtained by other the stethoscope systems 400.

Some implementations disclosed herein may be capable of providing authentication and/or identification functionality. For example, one of the servers 1165 of the data center 1145 may be capable of controlling access to information obtained by networked stethoscope systems 400. In some such examples, a server 1165 may provide access to such information only after a user has provided an authentic user name and a corresponding password, e.g., via the mobile device 920b or the laptop 1115, which have been accepted by the server 1165. The user name and password may have been established during a prior enrollment process.

According to some implementations, one or more of the devices shown in FIG. 11 may be capable of obtaining biometric information. For example, in some implementations the mobile device 920a, the mobile device 920b and/or the laptop 1115 may include a biometric sensor system, which may include a fingerprint sensor system, a camera system, etc. In some examples, a server 1165 may provide access to information obtained by networked stethoscope systems 400 only after a user has provided fingerprint information or other biometric information (e.g., via the mobile device 920a, the mobile device 920b or the laptop 1115) that has been authenticated by the server 1165. (As used herein, "fingerprint information" includes print information corresponding to any digit, including fingerprint images and thumbprint images.) The server 1165 may, for example, compare the provided fingerprint or other biometric information (also referred to herein as "currently-obtained biometric information") with stored biometric information that was obtained during a prior enrollment process (also referred to herein as "previously-obtained biometric information").

In alternative implementations, another device may be capable of providing authentication and/or identification functionality. For example, in some implementations, a control system 410 of a stethoscope system 400, a control system of a mobile device, or both, may include authentication and/or identification functionality.

In some examples, a biometric sensor system of the mobile device 920a, such as a fingerprint sensor system, may obtain biometric information from a user. Alternatively, or additionally, in some examples a biometric sensor system of the stethoscope system 400 may obtain biometric information from a user. A control system may perform an authentication process that is based, at least in part, on the biometric information in order to verify the identity of the user. For example, the authentication process may involve comparing currently-obtained biometric information with previously-obtained biometric information from an authorized user. Depending on the particular implementation, the control system may reside in the mobile device 920a, in the stethoscope system 400 or in another device (such as a server 1165).

If the authentication process is successful, in some implementations the control system may authorize a user whose identity has been verified to control the stethoscope system 400 via the mobile device 920a and/or to receive information from the stethoscope system 400 via the mobile device 920a. In some implementations, the data and/or other sensor data that are acquired by the stethoscope system 400 may be associated with identity information of the user. For example, the data and/or other sensor data that are acquired by the stethoscope system 400 may be stored in a data structure that also includes the identity information of the user. In some examples, the identity information may include the user's name. In some instances, the identity information may include at least some of the biometric information that was obtained during the authentication process, such as fingerprint information.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on one or more computer-readable media, such as one or more non-transitory media. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. A stethoscope system, comprising:
a patch that includes an array of pressure sensors and a user feedback system, the patch including flexible material that allows the patch to be conformed to a patient's body; and
a control system capable of:
receiving signals from the array of pressure sensors, the signals corresponding to measurements from multiple pressure sensors of the array of pressure sensors;
combining signals from multiple pressure sensors of the array of pressure sensors to produce combined signals;
filtering the combined signals to remove, at least in part, breathing signal components and to produce filtered signals; and
determining a correspondence between heart signal components of the filtered signals and corresponding heart valve activity, wherein the control system includes one or more components from a list of components consisting of: a general purpose single- or multi-chip processor; a digital signal processor; an application specific integrated circuit; a field programmable gate array or other programmable logic device, discrete gate or transistor logic, and a discrete hardware component and wherein the control system is capable of providing instructions, via the user feedback system, regarding placement of the patch on a patient's chest.

2. The stethoscope system of claim 1, wherein the control system is capable of transforming the signals from a time domain into a frequency domain.

3. The stethoscope system of claim 1, wherein the control system is capable of determining a quality metric for the heart signal components.

4. The stethoscope system of claim 3, wherein the control system is capable of providing instructions via the user feedback system based on a comparison of the quality metric and a quality metric threshold.

5. The stethoscope system of claim 4, wherein the user feedback system includes force feedback elements.

6. The stethoscope system of claim 5, wherein the force feedback elements include pressure sensors.

7. The stethoscope system of claim 6, wherein the force feedback elements and the pressure sensors are piezoionic devices.

8. The stethoscope system of claim 1, wherein the array of pressure sensors is a two-dimensional M by N or M by M array, wherein M and N are integers.

9. The stethoscope system of claim 1, wherein the control system is further capable of performing signal pre-processing before combining the signals.

10. The stethoscope system of claim 1, wherein the patch includes at least one layer of adhesive material for secure placement on the patient's body.

11. The stethoscope system of claim 1, wherein the patch includes flexible material to which the array of pressure sensors is attached.

12. The stethoscope system of claim 1, wherein the array of pressure sensors includes substantially identical pressure sensors.

13. The stethoscope system of claim 1, wherein the signals correspond to multiple simultaneous measurements obtained from different areas of a patient's chest during a time interval.

14. The stethoscope system of claim 1, wherein the signals correspond to multiple simultaneous and redundant measurements of vibrations produced by one or more heart valves.

15. The stethoscope system of claim 1, further comprising an interface system capable of wireless communication.

16. The stethoscope system of claim 1, further comprising an interface system, wherein the control system is capable of receiving instructions, via the interface system, and of controlling at least a portion of the stethoscope system according to the instructions.

17. The stethoscope system of claim 1, wherein the control system is disposed, at least in part, in another device.

18. The stethoscope system of claim 1, wherein the signals correspond to redundant measurements from multiple pressure sensors of the array of pressure sensors.

19. The stethoscope system of claim 1, wherein the control system is further capable of determining a correspondence between heart signal components and corresponding parts of a cardiac cycle.

20. The stethoscope system of claim 1, further comprising an interface system, wherein the control system is further capable of detecting an abnormality of heart valve activity and of transmitting a signal, via the interface system, corresponding to the abnormality.

21. A method of processing signals from a stethoscope system, comprising:
- receiving, by a control system, signals from a patch that includes an array of pressure sensors, the patch including flexible material that allows the patch to be conformed to a patient's body, the signals corresponding to measurements from multiple pressure sensors of the array of pressure sensors;
- providing instructions from the control system via a user feedback system of the patch, regarding placement of the patch on a patient's chest;
- combining, via the control system, signals from multiple pressure sensors of the array of pressure sensors to produce combined signals;
- filtering the combined signals, via the control system, to remove, at least in part, breathing signal components and to produce filtered signals; and
- determining a correspondence, via the control system, between heart signal components of the filtered signals and corresponding heart valve activity, wherein the control system includes one or more components from a list of components consisting of: a general purpose single- or multi-chip processor; a digital signal processor; an application specific integrated circuit; a field programmable gate array or other programmable logic device, discrete gate or transistor logic, and a discrete hardware component.

22. The method of claim 21, further comprising determining a quality metric for the heart signal components.

23. The method of claim 22, further comprising providing instructions based on a comparison of the quality metric and a quality metric threshold.

24. The method of claim 21, further comprising detecting an abnormality of heart valve activity and of transmitting a signal corresponding to the abnormality.

25. At least one non-transitory medium having software stored thereon, the software including instructions for:
- receiving, by a control system, signals from a patch that includes an array of pressure sensors, the patch including flexible material that allows the patch to be conformed to a patient's body, the signals corresponding to measurements from multiple pressure sensors of the array of pressure sensors;
- providing instructions from the control system via a user feedback system of the patch, regarding placement of the patch on a patient's chest;
- combining signals from multiple pressure sensors of the array of pressure sensors to produce combined signals;
- filtering the combined signals, via the control system, to remove, at least in part, breathing signal components and to produce filtered signals; and
- determining a correspondence, via the control system, between heart signal components of the filtered signals and corresponding heart valve activity, wherein the control system includes one or more components from a list of components consisting of: a general purpose single- or multi-chip processor; a digital signal processor; an application specific integrated circuit; a field programmable gate array or other programmable logic device, discrete gate or transistor logic, and a discrete hardware component.

26. The at least one non-transitory medium of claim 25, wherein the software includes instructions for determining a quality metric for the heart signal components.

27. The at least one non-transitory medium of claim 25, wherein the software includes instructions for detecting an abnormality of heart valve activity and of transmitting a signal corresponding to the abnormality.

28. A stethoscope system, comprising:
- a patch that includes an array of pressure sensors and a user feedback system, the patch including flexible material that allows the patch to be conformed to a patient's body; and
- control means for:
  - receiving signals from the array of pressure sensors, the signals corresponding to measurements from multiple pressure sensors of the array of pressure sensors;
  - combining signals from multiple pressure sensors of the array of pressure sensors to produce combined signals;
  - filtering the combined signals to remove, at least in part, breathing signal components and to produce filtered signals; and
  - determining heart valve activity based, at least in part, on the filtered signals, wherein the control means includes one or more components from a list of components consisting of: a general purpose single- or multi-chip processor; a digital signal processor; an application specific integrated circuit; a field programmable gate array or other programmable logic device, discrete gate or transistor logic, and a discrete hardware component and wherein the control system is capable of providing instructions, via the user feedback system, regarding placement of the patch on a patient's chest.

29. The stethoscope system of claim 28, further comprising an interface system, wherein the control means includes means for detecting an abnormality of heart valve activity and of transmitting a signal, via the interface system, corresponding to the abnormality.

30. The stethoscope system of claim 28, wherein the control means includes means for determining a correspondence between heart signal components of the filtered signals and corresponding parts of a cardiac cycle.

* * * * *